US008643842B2

(12) United States Patent
Cohen et al.

(10) Patent No.: US 8,643,842 B2
(45) Date of Patent: *Feb. 4, 2014

(54) METHOD AND SYSTEM FOR USE IN MONITORING PROPERTIES OF PATTERNED STRUCTURES

(71) Applicant: Nova Measuring Instruments Ltd., Rehovot (IL)

(72) Inventors: Yoel Cohen, Nes Ziona (IL); Boaz Brill, Rehovoth (IL)

(73) Assignee: Nova Measuring Instruments Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/652,513

(22) Filed: Oct. 16, 2012

(65) Prior Publication Data

US 2013/0096876 A1   Apr. 18, 2013

Related U.S. Application Data

(63) Continuation of application No. 12/596,670, filed as application No. PCT/IL2008/000966 on Jul. 13, 2008, now Pat. No. 8,289,515.

(60) Provisional application No. 60/949,034, filed on Jul. 11, 2007.

(51) Int. Cl.
*G01B 11/06* (2006.01)
*G01J 4/00* (2006.01)
*G01N 21/84* (2006.01)

(52) U.S. Cl.
USPC ........... 356/369; 356/368; 356/464; 356/630; 356/401; 250/548

(58) Field of Classification Search
USPC .......... 356/364–369, 630, 625, 401; 250/548, 250/559.3, 225
See application file for complete search history.

(56) References Cited

U.S. PATENT DOCUMENTS

| | | | |
|---|---|---|---|
| 6,392,756 B1 * | 5/2002 | Li et al. | 356/632 |
| 6,934,031 B2 * | 8/2005 | Kwon | 356/445 |
| 7,196,793 B2 * | 3/2007 | Nabatova-Gabain et al. | 356/369 |
| 7,202,958 B1 * | 4/2007 | McGahan | 356/630 |
| 7,259,850 B2 * | 8/2007 | Ke et al. | 356/369 |
| 7,301,163 B2 * | 11/2007 | Brill et al. | 250/548 |
| 2004/0185582 A1 | 9/2004 | Kueny | |
| 2004/0267490 A1 | 12/2004 | Opsal et al. | |
| 2005/0122516 A1 | 6/2005 | Sezginer et al. | |

FOREIGN PATENT DOCUMENTS

WO  03081662  10/2003
WO  2005067009 A2  7/2005

* cited by examiner

*Primary Examiner* — Sang Nguyen
(74) *Attorney, Agent, or Firm* — AlphaPatent Associates Ltd.; Daniel J. Swirsky

(57) ABSTRACT

A method and system are presented for use in characterizing properties of an article having a structure comprising a multiplicity of sites comprising different periodic patterns, where method includes providing a theoretical model of prediction indicative of optical properties of different stacks defined by geometrical and material parameters of corresponding sites, said sites being common in at least one of geometrical parameter and material parameter; performing optical measurements on at least two different stacks of the article and generating optical measured data indicative of the geometrical parameters and material composition parameters for each of the measured stacks; processing the optical measured data, said processing comprising simultaneously fitting said optical measured data for the multiple measured stacks with said theoretical model and extracting said at least one common parameter, thereby enabling to characterize the properties of the multi-layer structure within the single article.

20 Claims, 8 Drawing Sheets

| Correlation Analysis Rt | | |
|---|---|---|
| | L1. Thickns | L2. Thickns |
| L1. Thickns | - - - - - | 0.9995 |
| L2. Thickns | 0.9995 | - - - - - |

Sigma Value of L1. Thickness = 9.75
Sigma Value of L2. Thickness = 9.64

| Correlation Analysis Result | | | | |
|---|---|---|---|---|
| | L1. H | L2. Thickns | L1. CD | L1. A |
| L1. H | - - - - | 0.0198 | 0.6090 | 0.8595 |
| L2. Thickns | 0.0198 | - - - - | 0.0946 | 0.0082 |
| L1. CD | 0.6090 | 0.0946 | - - - - | 0.5018 |
| L1. A | 0.8595 | 0.0082 | 0.5018 | - - - - |

Sigma Value of L1.H = 1.95
Sigma Value of L2. Thickness = 0.39
Sigma Value of L1. CD = 0.90
Sigma Value of L1. A = 0.04

METHOD AND SYSTEM FOR USE IN MONITORING PROPERTIES OF PATTERNED STRUCTURES

CROSS-REFERENCE TO RELATED APPLICATIONS

This application is a continuation of U.S. patent application Ser. No. 12/596,670, filed Oct. 20, 2009, which is a U.S. National Phase Application under 35 U.S.C. 371 of PCT International Application No. PCT/IL2008/000966 which has an international filing date of Jul. 13, 2008, and which claims priority from U.S. Provisional Patent Application No. 60/949,034, filed Jul. 11, 2007, all of which disclosures are hereby incorporated by reference.

FIELD OF THE INVENTION

This invention is generally in the field of semiconductor industry and relates to a method and system for inspecting a patterned article (semiconductor wafer).

BACKGROUND OF THE INVENTION

There has been a long-standing need in the semiconductor industry to characterize the properties of a semiconductor device. As dimensions of devices in this industry are diminishing, increasingly sensitive metrology tools and analysis techniques are required for measurement of the properties of these devices, in particular, devices comprising a stack of thin films on a semiconductor substrate.

Optical metrology tools used for such measurements are typically ellipsometry and reflectometry based tools. Reflectometry based tools typically measure changes in the magnitude of radiation reflected/transmitted from/through the sample, and ellipsometry based tools typically measure changes of the polarization state of radiation after interacting with the sample.

Measured optical data, indicative of the detected radiation (reflected and/or transmitted), can be analyzed to derive information regarding the optical constants of materials included in the sample, as well as the layer parameters, such as thickness and geometrical parameters of patterns (including critical dimension (CD), line spacing, line width, wall depth, and wall profile).

Examples of the measurement techniques of the kind specified are disclosed in "Simultaneous Measurement of Six Layers in a Silicon on Insulator Film Stack Using Spectrophotometry and Beam profile Reflectometry", J. M. Leng at al., J. Appl. Physics, 81(8), 15 Apr. 1997, pp. 3570-3578; US 2006/0167651; U.S. Pat. No. 7,259,850; U.S. Pat. No. 5,999,267; and U.S. Pat. No. 6,091,485.

Also known are methods based on selective material removal from the full multi-layer structure, which are disclosed in U.S. Pat. No. 7,289,234 and U.S. Pat. No. 7,019,850 both assigned to the assignee of the present application.

GENERAL DESCRIPTION

The need for characterizing the properties, and particularly optical material properties (such as n, k being the real and imaginary parts of the complex index of refraction) of thin films, is required for various applications. The latter includes but is not limited to enablement of proper designs of patterned structures (such as wafers) suitable for a required performance in an electronic device and control of such properties during the structure production; and creation of data to be a pre-requisite for other optical measurements, e.g. scatterometry, which are sensitive to optical material properties.

However, while characterization of a single uniform film is rather straightforward, the task of characterizing material properties, with high accuracy, in a structure/stack that contains several different materials, is much more complex. Generally, obtaining sufficiently accurate measurements of these properties may dictate high spectral accuracy across a spectral range for each of the material layers. Utilizing a single measurement of a thin layer stack may provide a spectral measurement of the required accuracy indicative of the measured properties of a single unknown layer, however the measured optical data is usually insufficient for accurate determination of the material properties of each of the materials comprising the full stack with the required confidence level. It is particularly significant when the spectral responses of several of the stack layers comprising materials are highly coupled, as is the case for example when utilizing both BARC (bottom antireflective coat) and photoresist layers.

The common practice currently used in the industry in order to obtain sufficiently reliable material properties is comprised of measurements taken on several wafers using the "additive stack" methodology and analytical modeling of the material properties. By utilizing an analytical model for the material properties, a correlation between different wavelengths is obtained, thereby reducing the number of independent variables characterizing each material, and the correlations between these parameters can be significantly reduced. The "additive stack" methodology typically utilizes several short-loop blanket wafers which are created such that the first wafer contains only the substrate and a first film made of a first material, a second wafer contains the substrate and both first and second films of first and second materials respectively, etc. The total number of blanket wafers is dependent on the number of the unknown materials whose properties are to be measured and analyzed. The first material is typically analyzed based on the measurements of the first wafer only. The results are then used in order to reduce the number of unknown parameters on the second wafer from which only the material properties of the second material are extracted, and so on. This method frequently suffers from inaccuracy, since errors are carried over from one wafer to the next.

Utilizing the "additive stack" approach for diagnosing complex structures presents additional limitations associated with the following. In many cases, some of the material properties change during subsequent steps of the wafer's fabrication process. Consequently, characterization (by measurements) of the properties of a material as deposited on the wafer (as is generally the case when utilizing blanket wafers) does not necessarily provide an exact description of the material properties evident in the final structure of the wafer (or at a subsequent step of the process) in which the effects of different patterning steps on the structures are present. Typically, the effects of such subsequent steps (e.g. deposition of subsequent layers, patterning etc) on the material properties are neither measured nor considered when utilizing the additive stack method. Although both the analytical modeling and the additive stack based techniques might provide for obtaining material properties of complex structures, these techniques require the use of many specially designed wafers, lengthy measurement/analysis processes, and are time consuming while involving highly skilled experts.

Thus, according to a first broad aspect of the invention, there is provided a method for characterizing properties of an article having a multi-layer structure comprising a multiplicity of sites comprising different periodic patterns, the method comprising:

providing a theoretical model of prediction indicative of optical properties of different stacks defined by geometrical and material parameters of corresponding sites, said sites being common in at least one of geometrical parameter and material composition parameter;

performing optical measurements on at least two different stacks of the article and generating optical measured data indicative of the geometrical parameters and material parameters for each of the measured stacks;

processing the optical measured data, said processing comprising simultaneously fitting said optical measured data for the multiple measured stacks with said theoretical model and extracting said at least one common parameter, thereby enabling to characterize the properties of the multi-layer structure within the single article.

It should be noted that measurements in different stacks refers to a case of measurements in different sites (locations) and/or that of measurements at the same site (location) but at different process' stages and thus characterized by different stacks at the same location. For simplicity however, in the description below, both of such options will be referred to as "sites" or "test sites" or "areas", but it should be understood that these expressions generally mean "different stacks".

It should also be understood that at least two different stacks or sites used in the measurements may include one patterned and one unpatterned site (the so-called "solid site"); two different patterned sites; or two different unpatterned (solid) sites. The technique of the present invention can be used for monitoring/controlling the article manufacture process using measurements taken at different steps in the process. Accordingly, a minimal measured set in this method would be a single patterned site measured in two process steps and thus having two different patterns respectively.

It should be noted that optical properties of a stack/site under measurement are described by an optical response of the respective site to interaction with an optical beam and may include diffraction, interference etc. effects. When speaking about a patterned site, the diffraction effects would be dominant. For simplicity, in the description below the general expressions "optical properties" and "interaction with optical beam" are referred to as being associated with diffraction.

According to another broad aspect of the invention, there is provided a measurement system for use in characterizing properties of an article having a multi-layer structure comprising a plurality of periodic patterns, the system comprising:

an optical measurement unit adapted for carrying out optical measurements and generating optical measured data indicative of geometrical parameters and material composition parameters for a measured area on the article;

a control unit connectable to the measurement unit, the control unit comprising:

a memory utility for storing reference data comprising a theoretical model of prediction, said model being indicative of optical properties of different stacks in a multi-layer structure defined by geometrical and material composition parameters of corresponding sites, where said sites are common in at least one of geometrical parameter and material composition parameter;

a processor utility configured and operable for processing and analyzing the optical measured data, said processing and analyzing comprising simultaneously fitting said optical measured data for the multiple measured stacks with said theoretical model and extracting said at least one common parameter, thereby enabling to characterize the properties of the multi-layer structure within the single article.

According to yet further aspect of the invention, there is provided a system for use in characterizing properties of an article having a multi-layer structure comprising a plurality of different periodic patterns, the system comprising a control unit adapted for receiving optical measured data indicative of geometrical parameters and material composition parameters of a measured area on the article and comprising: a memory utility for storing reference data comprising a theoretical model of prediction, said model being indicative of optical properties of different stacks a multi-layer structure defined by geometrical and material composition parameters of corresponding sites, where said sites are common in at least one of geometrical parameters and/or at least one of material composition parameters; and a processor utility configured and operable for processing and analyzing the optical measured data, said processing and analyzing comprising simultaneously fitting said optical measured data for the multiple measured patterns with said theoretical model and extracting said at least one common parameter, thereby enabling to characterize the properties of the multi-layer structure within the single article.

The present invention discloses a technique for parameters characterization in general and particularly optical material property characterization of a wafer of multi-layer material stack. The method described herein utilizes optical measurements of a single wafer comprising multiple material layers and having a multiplicity of different stacks (sites), e.g. patterned areas of the wafer.

The present invention further utilizes a physical theoretical model defined for each of the structures that are measured and analyzed. These models are used to measure accurately the global parameters associated with the results of optical measurements. This is usually achieved using inverse regression fit techniques adapted to correlate the actual results of optical measurements of the sites with the prediction of measurement results of the various sites as given by the site's models and to optimize the models parameters such that the predicted results fit the measured results. This procedure provides optimization of the measured parameters to obtain accurate values of these parameters with high confidence level.

In some embodiments of the invention, use is made of a multiplicity of different stacks which are produced using most or all of the same materials. Such stacks are typically located at different test sites and may include the so-called "solid sites" being unpatterned sites/areas and different patterned sites areas including periodic patterns (in 2D or 3D) with different pitch, features shape and/or duty cycle. The test sites can be made specially for measurement proposes; or alternatively or additionally existing sites within the product region of the wafer can be used as test sites.

The present invention utilizes optimization algorithms (such as inverse regression fit algorithms) to characterize common (global) parameters of the test sites. Physical, theoretical models of the sites' characteristics are adopted and utilized for predicting the measurements optical response expected by each test site. These physical models are typically based on physical theories such as Fresnel equations for characterizing the optical response of solid sites and RCWA (rigorous coupled-wave analysis) initially developed by Moharam and Gaylord and disclosed in M. G. Moharam and T. K. Gaylord, J. Opt. Soc. Am, 71, pp. 811-818 (1981), or another Method for calculating diffraction from grating structures as disclosed in U.S. Pat. No. 6,657,736. The models are parameterized to enable fitting the model to the sites' parameters, such as line width or layer thickness and layers' material parameters.

Generally although global parameters, common for at least two sites are measured, local parameters not necessarily identical within the sites are introduced to enable breaking the correlations between the global parameters measured and to enable an accurate determination of the global parameters of interest.

It is not straightforward to obtain correct theoretical parameters fitted to the results of the measurements, particularly when the degree of correlation between the required parameters is high or when the sensitivity of these parameters of interest is significantly below the sensitivity level of other parameters. In such cases regular, known in the art methods, fail to distinguish the effect of these parameters, and thus poor confidence level of these parameters is typically achieved.

However, the inventors of the present invention have realized that utilizing a multiplicity of structures made on several test sites, in which several parameters are common for some of the structures (i.e. global parameters) and other parameters (local) distinguish these structures from each other, may provide higher sensitivity values and reduce the correlations of the global parameters of interest. This idea is beneficial for analyzing and measuring the values of the common parameters with higher confidence level and providing higher fitting values (typically measured by merit function) of the measured optical responses to the predictions of sites' characterizing models.

To this end, it should be noted that common, global parameters may comprise any of the parameters characterizing the sites, including the parameters characterizing the material properties, layer thicknesses and geometrical parameters (e.g. CD, duty cycle etc.) as long as these parameters are common to at least some of the test sites inspected.

The present invention further provides an optimization method for characterization of single wafer characteristics. The method exploits the benefits of analyzing and measuring global parameters by utilizing a multiplicity of test sites as described above and provides a systematic approach for optimization of multiple test sites measurements enabling an accurate fitting of the physical models of the test sites to the measured results, thus providing higher confidence levels for measurements of these parameters.

Further to the above, although any global parameter can be analyzed according to this method, the method is highly suited for measurements of the optical material properties of the materials comprising the sample. Typically, when measuring solid wafer structures the sensitivity of the measurements to the material optical properties may be well below the sensitivity to other parameters, such as layers thickness. Furthermore, for some materials the optical properties are highly correlated (such as the case with BARC and photoresist materials). For these reasons, accurate measurement of these properties is difficult with existing methods.

Generally, characterizing the material properties of a multi-layer material stack structures comprising several, different, materials poses several difficulties. Typically, the amount of data received by a single measurement of such stack of materials may be insufficient for characterizing the optical properties of all the materials comprising said stack. For example, a spectroscopic measurement of the complex refraction index (n+ik) of a material stack comprising M different materials with a required spectral resolution of N wavelengths across the spectral range provides for N (if only n or k are measured) or 2N (if both n & k are measured) data points. Characterizing the complex refraction index (n+ik) of all the different materials generally requires for 2*M*N independent data points and thus a single measurement provides insufficient data for an accurate determination of these properties. The present invention solves this problem by determining these parameters utilizing multiple measurements of several sites in which these parameters are common and further provides an optimization algorithm adapted to distinguish and characterize these parameters through the measurements results. Further to the above, said method, for characterization of material properties, enables determination of the said properties as they are evident at the final stage of the wafer fabrication. The method resolves many of the limitations of the standard methodology of additive stack and model based analysis described above.

Since the structures (test sites) have at least some distinguishing local parameters different from other sites (e.g. different geometrical parameters), the measurements of these sites and the predictive physical models provide different spectra and hence additional information is obtained that is not contained in the non-patterned areas. Since the same materials are present in all structures, it is valid to combine the information taken from all these different sites into a single optimization problem and solve for the material properties across different sites at the same time.

It is a further aspect of the current invention to combine measurements taken in several steps of the process, e.g. both before and after etch, deposition or polish, allowing for a wider variety of structures and allowing more information to be collected. By measuring the same site in several steps of the process, a multiplicity of spectra is obtained, which can also reduce the number of different measurement sites required in order to achieve the required amount of information to extract the desired global parameters. Hence another aspect of this invention is the measurement of a single site on a single wafer over several steps of the process thereby providing a multiplicity of measured data allowing said extraction of global parameters.

An additional aspect of the invention is the use of different measurements taken from different locations on the wafer representing somewhat different structures, e.g. due to center-to-edge variations which are typical of many processes (CMP, CVD).

It is a further aspect of this invention that use can be made of deliberate modifications done in one of the processes to increase the amount of information available for the optimization. For example, use can be made of the degrees of freedom allowed by a photolithography process that is one of the steps used for the production of the wafer. By exposing different fields on the wafer using different exposure and/or focus conditions, it is possible to create different grating structures in different areas of the same wafer, thereby significantly increasing the amount of information which can be collected from a single wafer even to the degree that a single site per field is sufficient.

It is a yet further aspect of this invention to provide a method for process control in which the material properties are periodically monitored during a production process using standard product wafers as opposed to the use of special wafers that require intervention of the standard process flow. By measuring a multiplicity of sites on standard process wafers and submitting the results to the analysis methods described in this invention, it is possible to continuously monitor the material properties of various layers in the process. The measured material properties can then be utilized e.g. for flagging changes during normal operation of process tools such as deposition chambers, for qualifying such process tools after periodic maintenance, etc. Since the simultaneous fitting of a multiplicity of sites is more, time consuming than a standard fitting process of a single measurement site, it is possible that the data for said multiple-site analysis is run as a separate, parallel process on the same processing unit or is sent for processing on a separate, potentially remote processing unit, thereby allowing the measurement system to provide a periodic material characterization analysis without delaying the continuous use of the same measuring system for standard single-site measurements.

This method provides several solutions to the issues that limit the standard method as described above. Since all structures are defined on the final layer, there is no need for producing short-loop wafers to create an "additive stack", thus saving cost and shortening the time-to-solution. Moreover, since all structures are produced from the full stack, all aspects of material changes after deposition are automatically taken into account. Additionally, since the only requirement is for the correct test sites (or within-product sites) to be present on the mask, this method allows following up on the material properties during serial production in the exact same way as done during the initial recipe setup, allowing better process control, which is impossible with the standard additive stack method. In order to further enhance the amount of available information, it is possible to measure the different sites using multiple measurement methods, e.g. measure polarized spectra or ellipsometric parameters at a multiplicity of incidence angles.

Clearly, the use of this method relies on the ability to model the diffraction from complex structures at various illumination conditions, however this capability is basically equivalent to the modeling capabilities required by scatterometry and are hence widely known. The difference is in implementing this modeling towards the characterization of material properties together with the geometrical parameters, whereas in previous works material properties are assumed known and the target is to optimize for geometrical parameters. The quality of the solution is largely due to the ability to correctly combine a large body of information without reaching the wrong solution, for example due to local minima of the fitting function.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 2A illustrates a non-patterned (solid) area; FIGS. 2B-2D illustrate several patterned sites with various pitch and duty cycle values in which the patterning is at the upper layer, e.g. typical of post development measurements in lithography; and FIGS. 2E-2F illustrate two patterned sites with various pitch and duty cycle values that may be measured at different steps of the process, e.g. after etching;

DETAILED DESCRIPTION OF EXEMPLARY EMBODIMENTS

Figure 1:
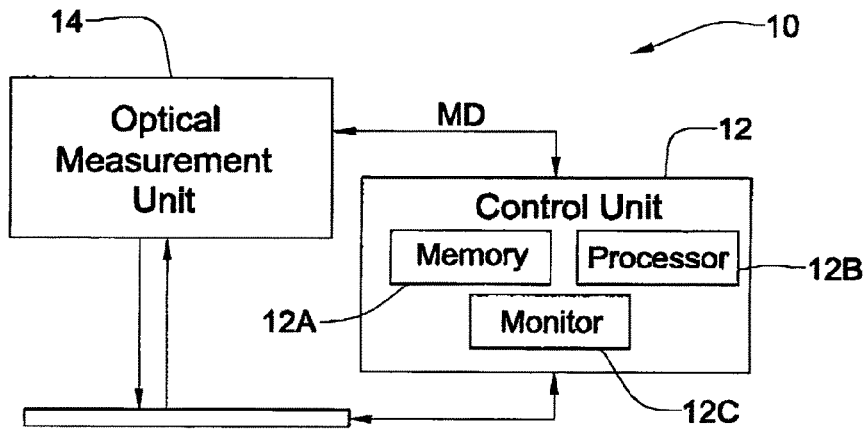
FIG. 1 is a schematic illustration of an example of a system suitable for carrying out a method of the present invention.

Referring to FIG. 1, there is schematically illustrated an example of a measurement system, generally designated 10, suitable to be used for implementing the technique of the present invention for monitoring (measuring/inspecting) the properties of a wafer W. The latter constitutes an article comprising a patterned structure. The article has at least two different stacks (e.g. within different sites), at least one of them having a periodic pattern; thus the article may have multiple patterned sites/areas (generally, stacks) and possibly also one or more unpatterned sites/areas (stacks).

The system 10 comprises a control unit 12 which is typically a computer system including one or more computers, each including inter alia a memory utility 12A, a processor utility 12B, a data presentation utility (e.g. monitor) 12C. The control unit is configured and operable for receiving and processing optical measured data MD, e.g. coming from an optical measurement unit 14. The measured data is indicative of the geometrical parameters and material composition parameters of one or more measured sites/areas of an article under measurement. To this end, the control unit utilizes a previously provided theoretical model of prediction. This model is configured to be indicative of diffraction properties of at least some of non-patterned and patterned areas on the article similar to that under measurement. The diffraction properties are defined by geometrical and material-associated optical parameters of the measured areas. The model assumes that the measured areas have common geometrical parameter(s) and/or material-associated optical parameter(s).

The theoretical model is previously appropriately selected and stored, e.g. in the memory utility of the control unit (e.g. being distributed between memories (databases) of different computers connectable to one another), or in a separate database accessible by the control unit via a communication network. It should also be noted that the measured data may be processed off-line, i.e. in a post-measurement session; or on-line (real time). The control unit 12 may be connectable to the measurement unit 14 via wires or wireless signal transmission.

The optical measurement unit 14 may or may not be the constructional part of the system of the present invention. The system of the present invention (control unit 12) is however configured to be capable of analyzing measured data obtained by a predetermined type of optical measurement. In other words, the theoretical model is selected to describe diffraction and/or interference properties of an article (similar to that under measurement) and measured according to a predetermined technique. The optical measurement unit may be configured for carrying out spectral ellipsometry or spectral reflectometry, preferably operable in a zero order diffraction detection mode. It should be noted that in some embodiments, the optical measurement unit might include measurement tools of different types, or in some other embodiment the optical unit may utilize the same measurement tool but operated with different measurement modes, to thereby carry out different measurements on the same or different sites on the article.

The control unit 12 (its processor utility 12B) is preprogrammed for processing the optical measured data. This processing includes simultaneously fitting the optical measured data for the multiple measured areas with the theoretical model and extracting at least one common parameter. This enables to characterize the properties of the multi-layer structure within the single article/structure. This is the so-called "Single Wafer Parameters Optimization" (SWPO) technique. Such a method may for example utilize a parallel regression fit algorithm for optimizing certain properties, typically optical properties, of certain materials/layers.

The SPWO technique can be used for characterizing properties of an article having a patterned structure (e.g. wafer), i.e. a structure which has patterned areas and possibly also one or more non-patterned areas (solid stack areas), keeping in mind that such "areas" constitute stacks associated with the same or different locations on the article. The method utilizes processing and analyzing measured data from a plurality of areas or sites, which thus serve as test sites and are located within a test region of the article outside a product region of said article or located within the product region. The areas can be described by their geometrical and material composition parameters. The areas typically differ from each other by some of the geometrical and/or material properties (i.e. local properties/parameters), while some of these properties are common for at least some of the areas (i.e. common/global properties/parameters).

A theoretical (physical) model is used to provide predictions indicative of the interference/diffraction properties of at least some of the different areas. More specifically, the model has multiple sub-models corresponding to different areas, i.e. areas different in the geometrical parameter(s) and/or material composition parameter(s). As indicated above, such diffraction properties are generally dependent on the area properties (e.g. geometrical and/or material parameters characterizing the area). Optical measurements are performed on selected areas to provide measured data indicative of the diffraction properties for each of these areas.

Then, simultaneous fitting is applied for multiple sub-models and their corresponding measured data pieces, e.g. inverse regression fit methods. This is typically achieved by an iterative alteration of the parameters of the theoretical sub-model until an adequate level of fit is achieved simultaneously for the measured areas as is further described below.

When an adequate level of fit is achieved for the sub-models and the respective measured data, e.g. defined by a predetermined value of the total merit function, the values of the common parameters in the measured areas can be extracted to be further used to characterize the properties of the article.

The technique of the present invention allows for characterizing the properties of the article by measurements taken from the single article, i.e. eliminating a need for comparing data measured from different similar articles. However, the invention is not limited to single-article measurements, and sometimes measured data to be processed is that collected from the measured areas located on two or more articles (wafers). In some embodiments of the invention, common parameters, common for at least some of the measured areas, can be optimized.

The theoretical model suitable to be used in the present invention may include for example a description of the spectral response of each site on the wafer (as a function of several parameters, such as material Optical parameters and geometrical or structural parameters (e.g. expressed by functional presentation of the complex refraction index of certain materials and its dependency on the wavelength, layers composition and thickness). Generally, a theoretical model of this type does not always accurately describe/predict the measurement results. This is due to some effects such as process variations that may change the nominal state and interactions or other interface effects between layers that are, usually, not fully included within the theoretical model of the wafer.

To this end, multiple measurements of several, generally not similar, blanket wafers (e.g. Additive stack approach) can be used to enable optimization of measurements by providing separate, independent measurements of certain parameters (e.g. by measuring a wafer containing a first layer, then a wafer containing first and second layers etc.) and to provide an optimized model better fitted to measurement results. SPWO however preferably utilizes measurements of a multiplicity of test sites/areas fabricated on a single wafer (or on several wafers having generally the same material and structural properties). Generally, each of these areas is made with different geometrical properties, for example such areas may comprise several gratings with different CDs (e.g. line width) and duty cycles or periods as will be exemplified further below with reference to FIGS. 2A-2F). SPWO utilized the geometrical parameters of each area to provide modeled prediction of expected measurement results (e.g. local sub-models).

In some cases, the test sites/areas and their geometrical parameters are specially designed to enable extraction and optimization of certain parameters of interest of the theoretical model characterizing the effect of the material optical properties and geometrical properties of the wafer on the measurement results. This optimization process can be performed using data gathered directly through the measurements results or indirectly through further analysis of the theoretical models. In some other cases, the measurements are carried out on several sites already fabricated on the desired wafer which are found suitable for the analysis of the desired parameters/properties.

Thus, measurement results obtained by measuring several test sites (e.g. patterned areas) of the same wafer can be used together to analyze and optimize common ("global") parameters of the theoretical model (such as the complex refraction index of certain layers/materials).

Different patterned sites formed on a wafer are usually differentiated by certain geometrical parameters (e.g. duty-cycle, CD, periods, etc) and certain material optical parameters (e.g. refractive index and extinction coefficient). On the other hand, these patterned sites, fabricated on the same wafer, have in common at least one global structural parameter (e.g. the thickness of under layers) or common optical constants of materials. These global parameters, being essentially the same in all sites measured on the same wafer, are used for modeling theoretically the measured properties (such as reflectivity) of different test sites.

The following is an example of the SWPO method of the present invention:

Optionally, the design/analysis and optimization of the geometrical parameters of the multiple areas is carried out. This procedure is aimed at appropriately selecting the areas/sites on the wafer to be used in measurements. This step can be done before designing a mask to be used for manufacturing the test sites. Alternatively, this step can be aimed at selecting some of the sites among a multiplicity of candidate measurement sites already existing on the mask/wafer. In both cases, the optimization of the design or selection of the test sites is performed prior to actual measurements (i.e. is performed offline) based on theoretical calculations and does not require actual wafers. In cases where this step is performed prior to the mask design, the theoretical calculation can be linked to DBM (Design Based Manufacturing) techniques which identify the sites, verify their matching to design rules and OPC (Optical Proximity Correction) rules. This step will be more specifically described below with reference to FIG. 3).

Thus, either after the above described procedure or without it, one or more wafers are provided (produced) containing a combination of sites, including multiple patterned and optionally also non-patterned (solid) site(s). When a sufficient variety of sites exists on the same article (which is usually the case with semiconductor wafers) then the use of a single wafer is sufficient for the purposes of the present invention.

Optical measurements are applied to some of the sites on the wafer using optical metrology tools. The type and variety of tools can be chosen on a case-to-case basis to measure various properties of the wafer within the measured sites, for example the reflectance spectra can be obtained at various polarization states or ellipsometric parameters measurements can be taken at a single or at multiple incidence angles. Measurements may also be taken at multiple steps of the process.

The so obtained measured data is processed for optimization of the material properties of at least some of the materials. The processing of the measured data is based on physical models and optimization algorithms as will be further described below.

The SWPO of the present invention can be used with two or more test sites comprising periodic gratings and possibly also solid (un-patterned) stacks, such that the test sites have at least one common parameter. Such test sites can be measured to obtain diffraction properties, and simultaneous optimization can be utilized. In this connection, the expression "simultaneous optimization" refers to a procedure of obtaining a fit (a desired degree of fitting) of the measured data and the theoretical sub-models for all (or the desired number) of the measured sites. Such a fitting may be realized by a total fit criterion such as a merit figure calculated as the sum of merit functions. Typically, several periodic patterns are used in parallel interpretation (simultaneous measurement).

Figure 2A:
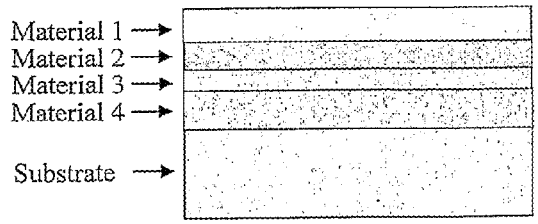
FIGS. 2A-2F are schematic diagrams showing a plurality of areas/sites of a single article sharing most or all of the same material stack.
Figure 2B:
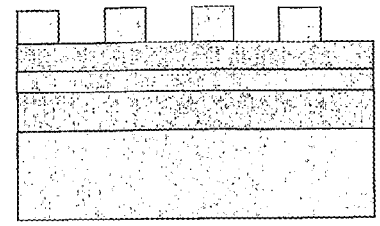
Figure 2C:
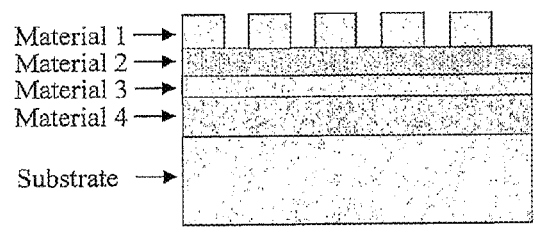
Figure 2D:
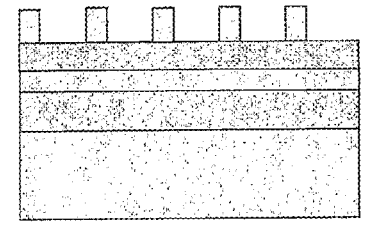
Figure 2E:
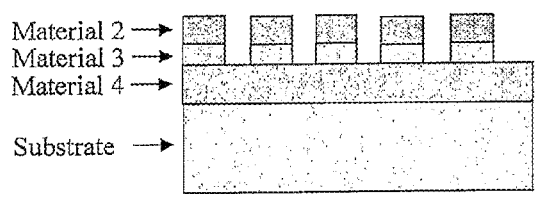
Figure 2F:
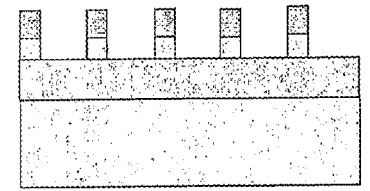

Reference is made to FIGS. 2A-2F illustrating schematically multiple sites (six such sites respectively) of the same wafer. Generally, the sites constitute different stacks, namely stacks different in one or more geometrical parameters (pattern parameters and/or layer thickness) and/or material-associated optical parameters, where such different stacks may be associated with different locations on the article or may result from different processing steps of the same location on the article. Thus, this wafer includes a non-patterned site (FIG. 2A) and several patterned sites (FIGS. 2B-2F) having various geometrical parameters such as pitch and duty cycle values. In the sites of FIGS. 2B-2D, only the uppermost layer is patterned and is in the form of spaced-apart regions of Material 1 on top of Material 2 layer. These sites can for example be used for post development measurements in lithography. The sites of FIGS. 2B-2D are different from one another in the pattern parameters and have common material composition parameters. In the sites of FIGS. 2E-2F, Material 1 is removed and two upper layers, Material 2 and Material 3 layers, are differently patterned. Thus, sites of FIGS. 2B-2F are also different from one another in the pattern parameters and have common material composition parameters. These sites may for example be measured after etching. In another option the patterns can be buried under additional layers deposited after the patterning.

Preferably, measurements are performed on close to one another sites in a single wafer. In these cases, the assumption that the global parameters, common for the measured test sites, possess similar values (e.g. common thickness of under layers or common stack materials parameters) is highly valid. This method can be performed without requiring specially designed wafers, or specially processed short loop wafers by utilizing suitable sites already made on an existing wafer.

In some cases, where different conditions exist on different locations of the wafer, measurements of different locations (e.g. test sites) may provide for additional information. For instance, when using a focus exposure matrix, the additional measurement information, to be processed in parallel, is associated with different focus and exposure conditions. Yet another option is working with different modes of operation of the same measurement tool such as different NA (numerical aperture) conditions.

Figure 3:
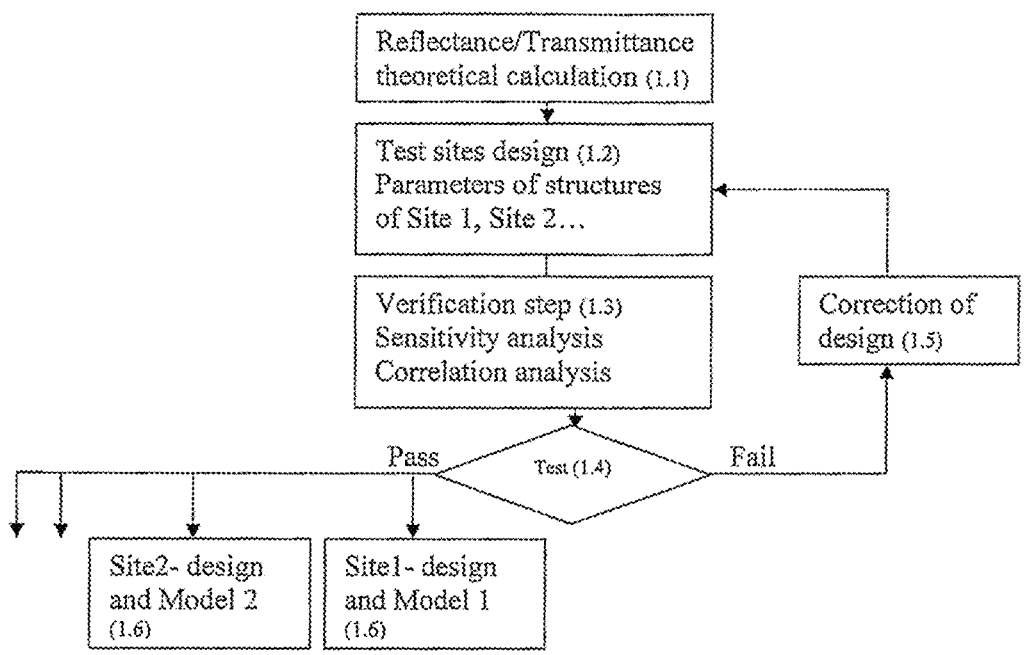
FIG. 3 is a flow diagram exemplifying an optional stage of preliminary designing the test areas.

Reference is made to FIG. 3 exemplifying an optional step of preliminary design of test sites. According to certain embodiments of the invention, different sites on the wafer are designed or selected to serve as a test site for measurements and optimization stages as noted above. This is a preliminary stage for the main optimization stage. This preliminary stage utilizes the ability to create a number of simple test sites (step 1.6) of patterned structures (periodic structures) and possibly also solid structure(s) on the wafer, via a mask design. In this stage, the desirable geometrical properties of the test sites are carefully analyzed and chosen according to the sensitivity of the parameters involved (i.e. to be measured or optimized) to variations of said geometrical properties and according to the degree of correlation between the effect of various geometrical properties to the measurement of the parameters involved. It is desired that the variations between the test sites would provide an independent (or loosely correlated) indication of the parameters involved to thereby enable estimation and optimization of these parameters through the results of the measurements of the test sites.

Thus, this stage enables a control of the test sites, to be measured, by careful mask design or careful choice of sites existing on a mask with emphasis on the sensitivity of the parameters involved.

An appropriate theoretical model (global model) is provided (step 1.1) including prediction of the materials involved and their properties (e.g. optical properties, reflectance/transmittance) and an optional design of periodic/patterned test sites (such as gratings), typically with several degrees of freedom (e.g. period and duty-cycle (line-space ratio)) varying for different test sites. An example of a global theoretical model characterizing a blanket wafer may include a set of equations determining the expected complex refraction index $(n(w)+ik(w))$ of the wafer and the dependence of said refraction index on several parameters characterizing the wafer such as the material composition of the stack and the thickness of the layers. It should be understood that different models are created for analysis of different properties as required in the specific optimization problem at hand. Several test sites are designed or chosen from an existing mask (step 1.2). The design includes specification of the geometrical properties characterizing the sites and generation of a site-model (i.e. local model or sub-model corresponding to each site), based on the global model obtained at step 1.1, for each of the test sites. The primary goal of design of said test sites is that the measurements of said sites would provide adequate sensitivity of the respective model to the optimized parameters and minimal correlations of those parameters to the other parameters involved in the model. Thus, the sub models (site models) provide prediction of the expected measurement results of the sites. These sub-models are typically based on the global model described above with the addition of each site's geometrical parameters.

The design of the site is then verified (step 1.3). This includes sensitivity and correlation analysis based on the theoretical model. As indicated above and will be further described, at this stage the test sites are analyzed for their sensitivity to variations of certain parameters of interest. To this end, sensitivity is defined as a ratio between the expected effects in the measured data (e.g. the change in the spectral transmittance/reflectance) that is caused due to a variation of the parameter under test (a change of fraction of the range of said parameter). This measure for sensitivity takes into account noise effects that may also affect the measured data, thus a sensitivity analysis can be evaluated relative to typical deviation of the measured quantity caused by noise. It is required that at least one of the test sites shows adequate sensitivity to a variation of a parameter of interest. A correlation analysis, also performed in this step, measures the degree of correlation between the sensitivities (as defined above) of the different test sites to variation of certain variables/parameters of interest. This is made to ensure "orthogonality" of these parameters with respect to the chosen test sites and to enable deduction of each of the parameters of interest based on measurement results of the test sites chosen, and to ensure the final precision and stability in extraction of each parameter. This correlation analysis will be more specifically described further below.

The sensitivity and correlation values of each of the parameters are tested against a threshold of the required final precision (step 1.4). When unsatisfactory precision values are obtained, the process starts again, from step 1.5, providing corrections to the design of the test sites.

The verification step 1.3 ensures that the sensitive parameters do not suffer from cross talk that can prevent the separate optimization. Such analysis allows for designing the best solution using predetermined structures. The use of such an initial analysis might be important even in the case where mask structures are not or cannot be designed. In this case, a high level of confidence might be needed prior to starting of the fit and thus an understanding of the level of errors in parameter optimization is critical.

When an appropriate design of the test sites is achieved and the error values obtained in step 1.4 are below the predetermined threshold or otherwise minimal, the set of test sites and corresponding local (site) models or sub-models are obtained (step 1.6).

Figures 5A, 5B:
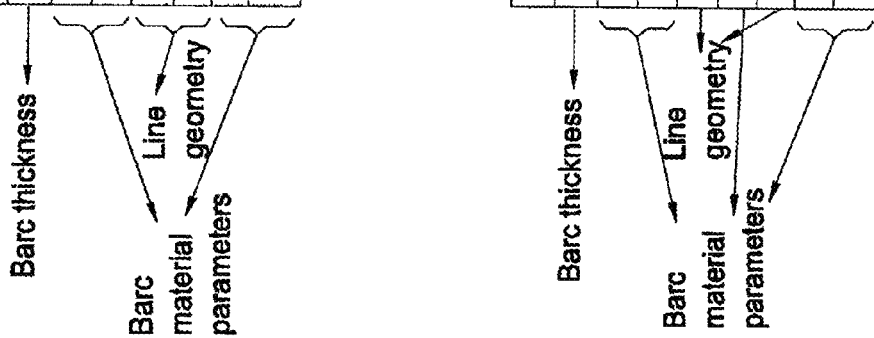
FIG. 5A shows a typical sensitivity analysis table of a patterned area with CD=45 nm and duty cycle of 1:1 (equal line to space)
FIG. 5B shows a typical sensitivity analysis table of a patterned area with CD=45 nm and duty cycle of 1:5 line to space.
Figure 5C:
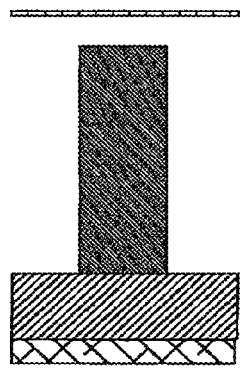
FIG. 5C illustrates a typical structure under investigation in FIGS. 5A and 5B.

Turning now to FIGS. 5A-5C there is shown an example of the sensitivity analysis. FIG. 5C shows a typical photoresist grating, e.g. photoresist line on top of BARC (Bottom Antireflective Coat) on Silicon substrate. FIGS. 5A and 5B show tables presenting sensitivity analysis of two test sites comprising photoresist gratings (of FIG. 5C) fabricated with different geometrical properties. FIG. 5A shows sensitivity analysis of a first test site with line width (i.e. CD) of 45 nm and duty cycle (i.e. line to space ratio) of 1:1 and FIG. 5B shows sensitivity analysis of a second test site with the same line width but with a duty cycle of 1:5. In the tables shown in these figures several material characteristics (parameters) and geometrical parameters characterizing the test sites are arranged in decreasing order of sensitivity. As can be seen, some material parameters are sensitive at the same level as geometrical parameters.

However the sensitivity values depend on geometrical (grating) parameters such as the duty-cycle or period. This dependence is exemplified in the comparison between the tables of FIGS. 5A and 5B that are calculated for different duty cycles. As can be seen from the tables, in this example both the sensitivity values assigned to each parameter and the order of sensitivity of different parameters depends on the duty cycle. This also supplies a first indication that each one of the parameters that are used in the optimization process is sensitive enough with respect to the noise level and to the changed parameters.

Figure 6A:
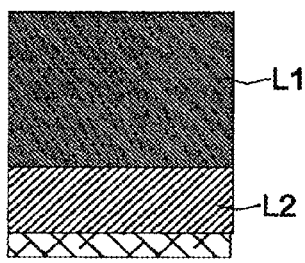
FIG. 6A illustrates parameter correlation matrix of a solid (un-patterned) area that exemplifies high correlation between the parameters.
Figure 6B:
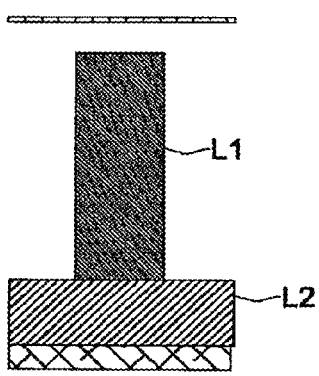
FIG. 6B illustrates parameter correlation matrix of a patterned (grating) area that exemplifies low correlation between the characterizing parameter.

A typical correlation analysis is illustrated in FIGS. 6A and 6B showing two cases of a wafer comprising a stack of two layers (marked L1 and L2 in both figures) and the corresponding variance and correlation tables (e.g. using covariance matrixes) illustrating the correlation/coupling between the parameters and the predicted variance of measurement of the parameters involved (in units of one sigma standard deviation). The wafer of FIG. 6A comprises a solid two-layer stack and the wafer of FIG. 6B comprises a simple equal line space grating.

In FIG. 6A, two structural parameters, the thicknesses of the first and second layers (marked L1.Thickness and L2.Thickness), characterize the solid wafer stack. A table of correlation analysis (shown in FIG. 6A, typical analysis from covariance matrix) characterizing the sensitivity of the measurements to variations in these parameters shows that the correlation between these parameters is strong (i.e. very close to unity, 0.9995) hence the conclusion that any one specific parameter cannot be accurately predicted through the results of measurements of this structure. As shown, for a given confidence level, a measurement error (sigma value) for thicknesses of layers L2 and L2 are respectively 9.75 and 9.64, which are relatively high due to the high correlation between the parameters.

FIG. 6B presents a method used according to the present invention to overcome the limitation presented by the high correlation of these parameters. A change of the structure characteristics, such as period and duty-cycle, is performed to a level that will enable distinguishing between parameters due to a reduction of the correlation between these parameters resulting from the changed/added geometrical features. As shown in FIG. 6B a grating structure is presented, patterned on the top layer (L1) and additional parameters are added (the line width marked as L1.CD and the wall angle marked as L1.A) corresponding to the grating geometry (the parameter L1.Thickness in FIG. 6A is substituted with L1.H the line height) in FIG. 6B. As evident from the correlation table shown in FIG. 6B the sensitivity correlation between the layers thicknesses that was high (0.9995) in the case of FIG. 6A is now reduced dramatically, in the case of FIG. 6B, to a value of (0.0198) which enables prediction of these parameters through the results of measurements of this structure. Comparing data in FIGS. 6A and 6B, it is evident that the lower degree of correlation reduces the measurement error for the layers' thicknesses.

It should be noted that the basic engine of such a correlation analysis can be the known variance-covariance method, but it can also be any other mathematical measure for correlations.

Hence, FIGS. 6A and 6B show a simple typical example in which use of a properly designed grating structure can enable differentiation in measuring two thickness parameters which are otherwise inseparable due to correlation between the parameters in a solid stack.

After implementation of the designed test sites on a mask (or alternatively choosing sites already existing on a mask or a wafer) and manufacturing of wafers, reflectivity measurements are performed. The information collected through the measurements of these sites is processed according to the process flow illustrated in FIG. 4 and further discussed below. Such information may comprise for example the spectral response values of reflectance at different sites or with different measurements parameters such as irradiation or measurement angles.

Figure 4:
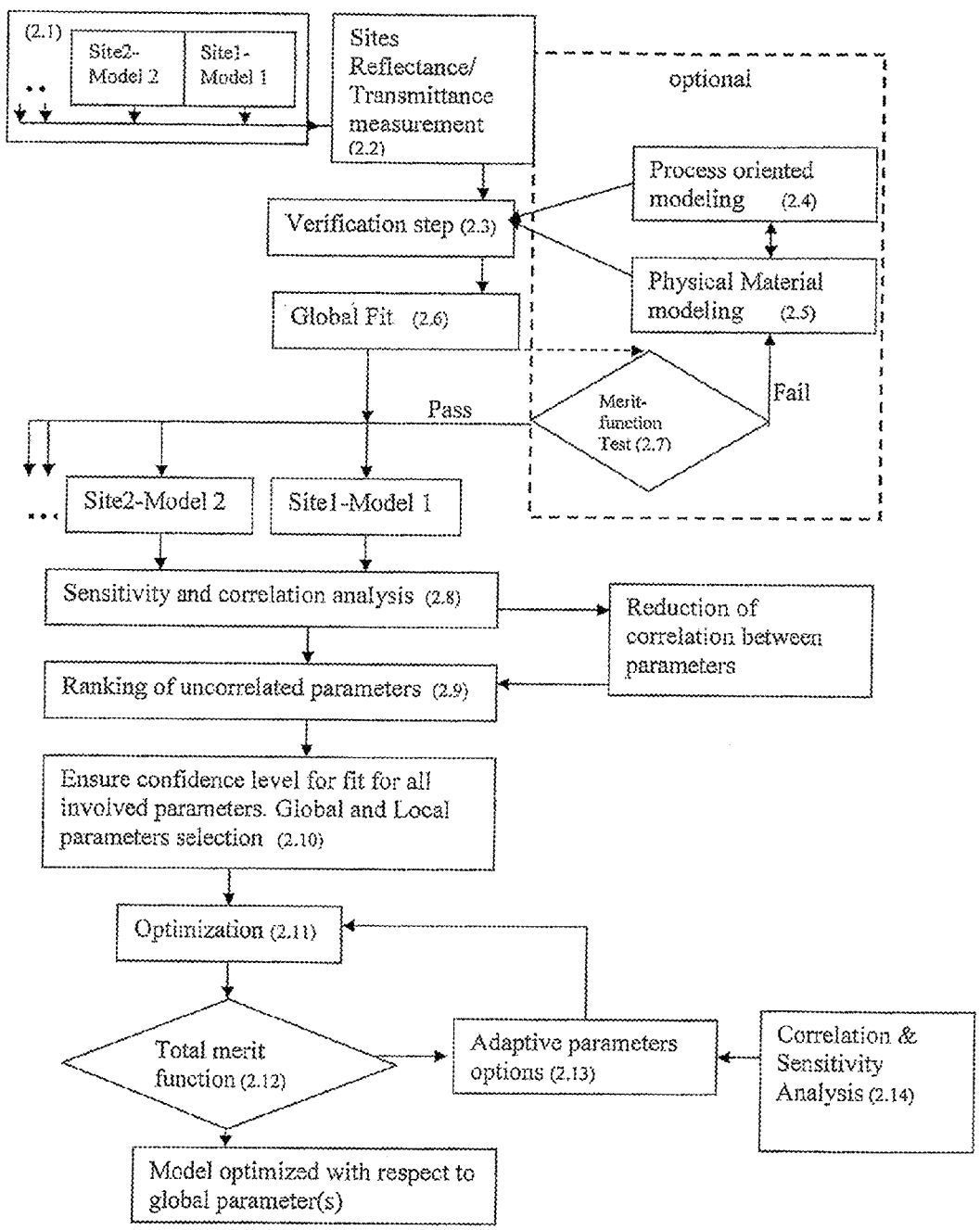
FIG. 4 is a flow diagram exemplifying an embodiment of the parameter optimization technique of the present invention.

FIG. 4 illustrates, in a way of flow diagram, an optimization stage process according to some embodiments of the present invention. The operation of this stage is based on utilizing and measuring existing sites which are present on a wafer. As indicated above the preliminary test sites design/analysis stage can be utilized to choose between available structures on the wafer/mask or a design of customized sites in order to obtain a set of measurements which can enable the required parameter separation.

Initially, in step (2.1), a wafer (typically one wafer on which the required test sites are made) and the location of the chosen test sites is supplied. A theoretical model of the wafer and a series of sub-models (local) corresponding to the test sites are obtained. Basically these models are either given as an input from the optional preliminary design stage (described above with connection to FIG. 3) or they are created at this stage.

A series of measurements (typically reflectance and transmittance measurements) for characterizing the optical properties of the test sites are carried out and the information comprising the measurements results is obtained in step (2.2).

A verification (step 2.3) is performed to ensure that the assumptions of the theoretical model are in agreement with the measurement results and that there is a degree of similarity between the results predicted by the model and the measurements. In case that the differences between the predictions of the theoretical model and the measurements are too large, the local parameters of the sites are adjusted and optimized (steps 2.4, 2.5). After the predictions of theoretical models (and the sub-models) are in good agreement with the measurements results, parameter verification (step 2.3) can be performed. Generally, these steps are optional and are aimed at verifying that the sub-models accurately describe the wafer and the test sites located thereon. This may be achieved by analyzing the deviations (that might occur in production) of the global and local parameters from the design and altering the theoretical model accordingly. To this end, the term global/common parameters refer to the structural and material parameters (e.g. differences in the layer widths) common to at least some of the test sites of the wafer. The term local parameters refers to the geometrical parameters different in the measured test sites.

Steps 2.4-2.7 of the flow diagram present an optional preliminary optimization process aimed at the adjustment and optimization of the local parameters (not common) and optionally also global parameters of each of the sub-models and corresponding test sites. Any inverse method technique such as library search or injection (as described e.g. in U.S. Pat. No. 6,657,736 or US 2004/0042017 assigned to the assignee of the present application) are options to be used here as well.

Thus, the parameter verification process is carried out by two steps: geometry variation and material properties variation. In a geometry verification (step 2.4), careful analysis is performed for proper geometry description of the sites. A simple approach is the use of trapezoidal shapes, and in increasing the number of the trapezoids in order to better cover the grating-shapes involved. It is preferable to use a "process oriented approach" in which basic knowledge and description of the process influence on the geometry parameters, allows better efficiency in the number of parameters and degrees of freedom required to define the structure.

The materials properties variation consists of materials physical modeling (step 2.5), implementing optimal mathematical modeling according to solid state physics materials knowledge, such as energy-gap and density of states.

During processing steps 2.4 and 2.5, the theoretical model and the sub-models are altered accordingly to reflect more accurately the actual parameters of the wafer and test sites as verified in these steps. Preferably, parameters are altered in each of the sub-models to provide better level of fit of each of the sub-models with the measurements of the corresponding test site and without impairing the fit level of other sites (i.e. by not changing global parameters common to these sites). After preparing models for a proper description of each of the test sites, a best fit of measured spectrum to the calculated spectrum based on the model should be achieved (step 2.6). In this case a specific pass/fail level of fit is defined for a merit function condition (step 2.7). This also verifies that sufficient degrees of freedom are implemented. After passing the single structure verifications, a multi-parameter global fit search is optionally performed on each of the structures to get the best possible suggestions for the starting point of the optimization of the global parameters (step 2.6). This minimizes any ambiguity. By performing it on several sites/stacks and using the commonality of results between all sites, the correct global minimum and best starting point is found.

Optionally, a measure (e.g. merit function) of the fit of each of the sites to the corresponding sub-model is tested against a predetermined threshold (step 2.7). When the fit level is insufficient and the global fit fails, the process might commence again from step 2.3 until a desired fit level is achieved.

When an adequate fit level is achieved, an optimal starting point models (global and accordingly site-related sub-models) are obtained with a good agreement of prediction to the measurement results. This ensures that the models do not fall within a local minima of the fit function and thus that the subsequent optimization processes would provide better accuracy.

In the next stage, the optimization process utilizes the starting point models to further optimize the global model by using regression fit methods and fitting the model with the measured results. The optimization/fitting method (e.g. regression fit) is performed by fitting a group of parameters at a turn in an order calculated according to the measured property sensitivity and according to the independency of the effect of the parameter-associated property on variations of other parameters. This ensures that the first parameters to be optimized within the model provide the highest contribution to the fitting function but are less affected by subsequent optimizations of other parameters.

Sensitivity and correlation analysis are then performed (step 2.8) based on the new starting point models in a similar way as described in step 1.3 of the preliminary design stage and exemplified in FIG. 3.

In the subsequent steps a regression is performed in which the parameters are repeatedly perturbed and the model is repeatedly evaluated to minimize the differences between the modeled results and results that have been empirically obtained. In order to perform the regression algorithm efficiently, sensitivity and correlation analysis follow, at step 2.9, by ranking the estimated contribution of the different parameters. The ranking signifies the importance and significance of the parameter. Parameters with higher ranking are included in the first steps of the regression, while others are included in the subsequent steps to thereby enable first optimizing parameters with higher influence on the fitting but with lower sensitivity (correlation) to subsequent variations of other parameters in the model.

The ranking of the parameters and the order of regression is chosen to ensure sufficiently narrow confidence intervals in the model parameters and parameter correlation tables and enables to estimate the match between theoretical data (calculated from the model) and the measured data (step 2.10). In some cases, the other measured data may be used to ensure higher level of confidence. For example, incorporating and/or omitting measured data of various wavelengths from the regression fit procedure, etc. Then, an increasing number of parameters is successively incorporated in the optimization (steps 2.12 and 2.13), which is done either manually or by an automatic algorithm. The definition of the steps for including additional parameters is based on the level of achieved fit versus the calculated sensitivity.

To this end, the level of achieved fit is measured, e.g. by the total merit function. In this embodiment, the sum of squared differences between the measured data and the model predictions are calculated for each of the test sites to provide a fitting value (e.g. merit figure) for each of the sites. The sum of the sites fitting is calculated as a total merit function. When the level of fit reaches some stopping criterion (step 2.12), the model and associated parameters are assumed to accurately reflect the measured data. One such stopping criterion is that the fit level (e.g. the total sum of the merit function of the test sites) reaches some predetermined level. Another criterion is reached when the reduction of the fit level becomes sufficiently small.

Other adaptive options can be implemented during the fitting process for better calculation time efficiency including varying the number of wavelengths, using a progressively increasing number of diffraction modes and increasing the density of angles describing the illumination conditions (step 2.13).

A correlation analysis (step 2.14) is used to identify which sites are preferable as starting points and which ones minimize the cross correlation in such a way that the confidence level achieved for each parameter is improved. This analysis is performed at the start, each time an additional parameter is added and prior to including an additional stack/site in the optimization process. With the progress of the optimization, more and more parameters with lower sensitivity are included and a better fit is achieved.

At some point, if the intermediate steps exhibit increasing deviations from the starting point, based on excessive parameter variation and high level of merit function convergence, the stacks geometry and material composition can be remodeled and the process restarted.

The optimization step of this algorithm (2.11) can utilize Inverse Regression techniques or other similar techniques such as iterative search for the least square minima e.g. Simplex or Levenberg-Marquardt algorithms. If calculation time is not a limitation, and the method cannot overcome local minima, Global search algorithm can be applied (e.g. Simulated annealing or Branch and Bound methods).

It should be noted that as the method described above with reference to FIG. 4 can be utilized as a baseline for total automation of the scatterometry modeling. The basic idea here is to have link for the mask data of the different sites and use some simple default assumptions for the verification steps 2.4 and 2.5. The following self correction loops are thus allowed: a starting point enhancement loop (steps 2.3, 2.6, 2.7, 2.4/2.5) and an improvement loop for the global parameters (steps 2.11, 2.12, 2.13). This way, existing mask information and basic modeling assumptions will be refined at first for the local sites and subsequently for global (common for these sites) parameters. The manual involvement in this case can be minimized and full automation can correct the initial assumptions.

The method can be applied to scatterometry overlay targets where different gratings exist on the wafer and may serve for the starting point for step 2.1. This relates to target design, moreover, the high accuracy of material models coupled with common lateral shifts in the targets can enable simultaneous analysis of overlay shifts during in-line monitoring. This is due to the natural case of different periods in scatterometry overlay targets (as compared to CD scatterometry). In this case, it is obvious that these targets are different structures that can be used for optimization. Another mode of work using scatterometry overlay targets is the use of different deliberate shifts in such targets to enable measurement of overlay. In this last case, each difference is in design and thus provides additional optical information that can be used by the method as different structure.

Figure 7A:
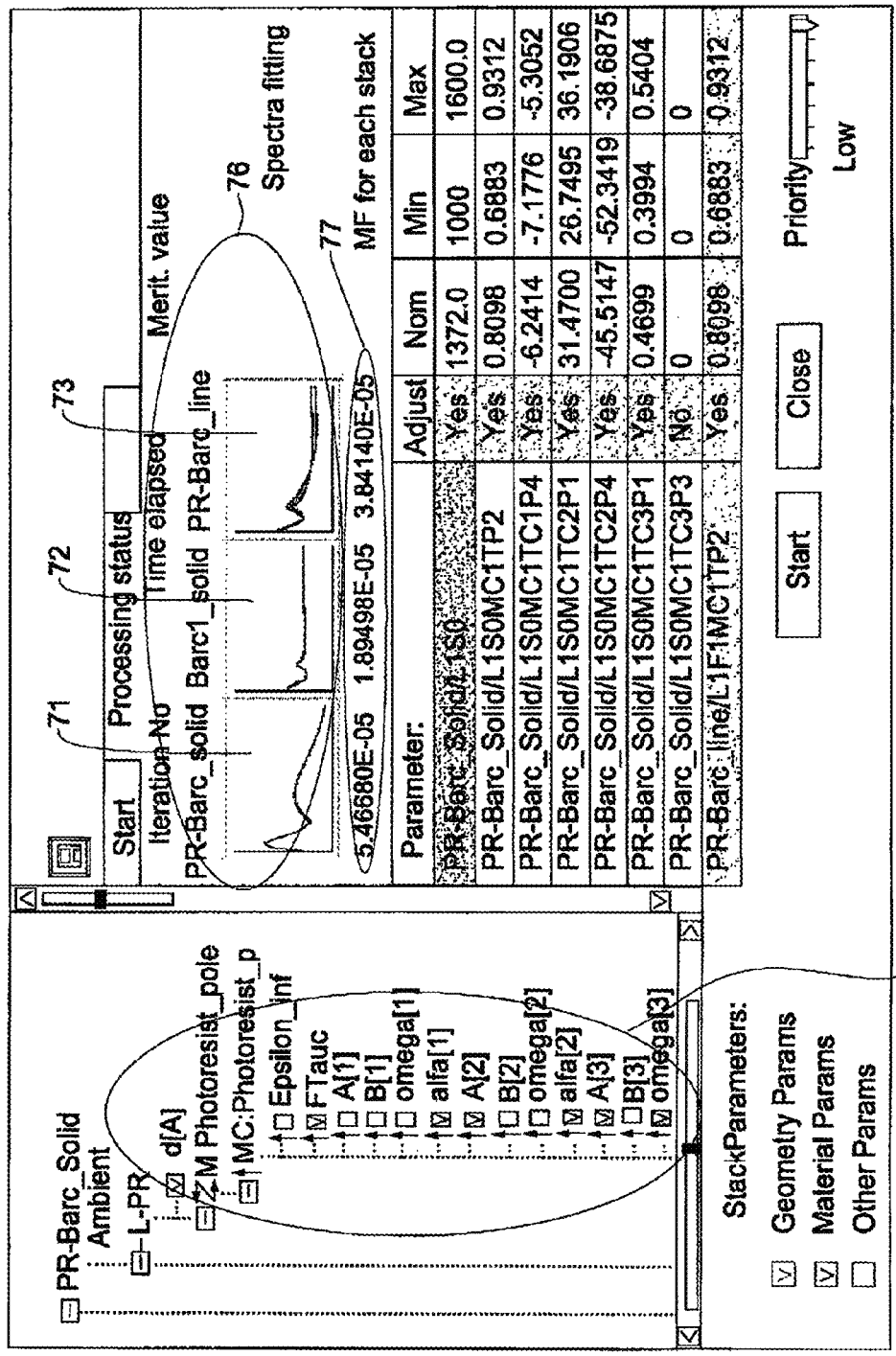
FIGS. 7A and 7B exemplify spectra fitting during two successive steps of the model optimization procedure, respectively, for three typical sites in lithography: Solid Photoresist layer on Barc layer on Silicon substrate, Solid Barc Layer on Silicon substrate, and grating of Photoresist on Barc layer on Silicon substrate.
Figure 7B:
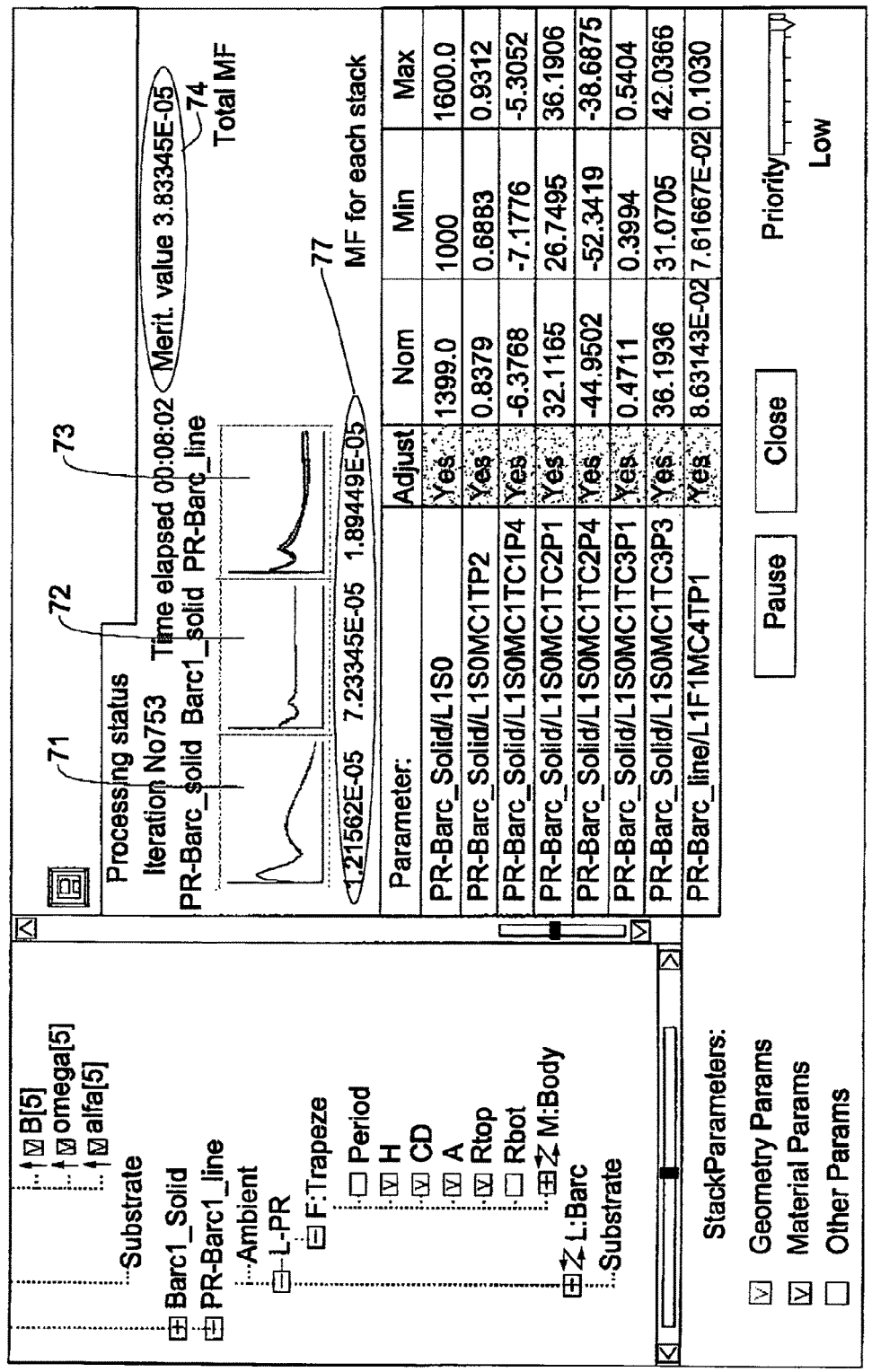

Turning now to FIGS. 7A and 7B, a typical spectra fitting for three typical sites in shift step is known and lithography is exemplified. The same numbers are used to identify the sites in both figures. A first site 71 is Solid Photoresist layer on Barc layer on Silicon substrate, a second site 72 is Solid Barc Layer on Silicon substrate, and the third site 73 is grating of Photoresist on Barc layer on Silicon substrate. FIG. 7A shows a typical situation during the optimization process. The parameters of the optimization are selected according to their sensitivity values (screen region 75). A diagram 76 for the measured data curves versus the theoretical prediction curves are shown for each of the sites analyzed and the fitting value 77, i.e. the merit function of each of the site, is shown. The total merit function, i.e. the sum of the sites merit functions of FIG. 7A (not shown) is about 11.19 E–05.

FIG. 7B shows the spectra fitting state of the parameters after optimization process is completed. The total merit function 74 is reduced to 3.83 E–05.

Figure 8:
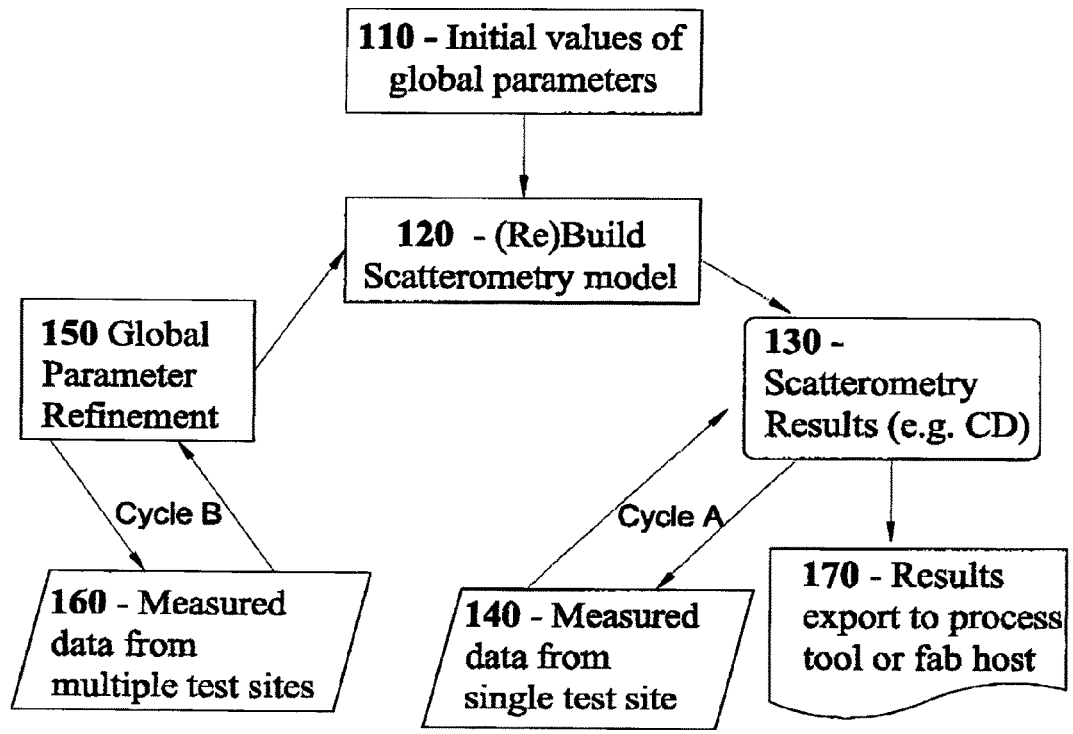
FIG. 8 shows a flow diagram of two parallel processes control procedures, according to an example of the present invention.

The technique of the present invention can also be used for automatic refinement of material parameters and other common parameters by applying the SPWO method on measurements performed in serial production thus enabling improved process control. FIG. 8 illustrates a flow diagram of a possible implementation of a process control. In this implementation, two control process cycles A and B are carried out concurrently during the production stage. Both cycles utilize measurements taken on standard production wafers. Cycle A is the standard, fast process control cycle in which a previously defined existing scatterometry model (step 120) is used for obtaining theoretical scatterometry data and using this data for the interpretation of measurements (step 130). To this end, measured data is provided (e.g. during the production process)—step 140; this data typically comes from a single site (or a small group of sites). Such a procedure (cycle A) can be used for process control of geometrical parameters, e.g. CD. The second, longer process control cycle B utilizes measurements taken on a large number of test sites as input data from the same standard production wafers (step 160). The number of required sites to be measured is typically larger than the number of sites used in cycle A. These measurements are then interpreted (step 150) according to the above-described SPWO methodology for the optimization of global (common) parameters such as material parameters and/or geometrical parameters. Cycles A and B processing procedures can be implemented by different software modules of the same or different processor utilities, the cycle B being typically a separated, longer control loop procedure. The results of cycle B can be continuously fed into and refine the scatterometry model in order to follow up on changes in global parameters, e.g. material properties. Alternatively, these results can be used for flagging process problems. In case that library is used for the interpretation of cycle A, the detection of significant deviation of global parameters in cycle B may automatically trigger the rebuilding of the library. Another option is to implement cycle B to collect data from cycle A using the same site(s) and to utilize the natural variability of the data typically occurring due to changes in some of the parameters as a function of time or coordinate across the wafer. Further option for implementing the SWPO method would be instead of measuring a multiplicity of test sites with different geometrical parameters, to create the required variability in the measured data using variable process conditions across the wafer, e.g. focus exposure matrix.

The SPWO method of the present invention can be used in a specific case as High-K metal gate (HKMG) application. In this case, the analysis of materials that are under the poly layers cannot be characterized very well. The reason for a characterization difficulty is that the PolySilicon layer becomes opaque in the UV. The analysis in the traditional additive stack is limited because thermal conditions and crystallinity of PolySilicon influence the Metal under the Poly and Poly crystal growth as well. Since the final process steps that include the thermal cycles and amorphization are normally done after the lithography steps, the optical characterization is not possible on blankets or solids. Moreover, the opaque nature of PolySilicon prevents any material characterization in the UV region using the additive stack option.

What is claimed is:

1. A method for characterizing properties of an article having a multi-layer structure comprising a multiplicity of sites comprising different periodic patterns, the method comprising:
    providing a theoretical model of prediction indicative of optical properties of different stacks defined by geometrical and material parameters of corresponding sites, said sites being common in at least one of geometrical parameter and material parameter;
    selecting one or more parameters of the article to be used for optimizing said theoretical model, the selecting comprising analyzing sensitivity of said theoretical model to variation of each of the selected parameters, analyzing correlation between said selected parameters, and upon identifying that the correlation does not satisfy a predetermined condition, changing at least one of the geometrical parameters of one of the stacks;
    performing optical measurements on at least two different stacks of the article and generating optical measured data indicative of the geometrical parameters and material composition parameters for each of the measured stacks;
    processing the optical measured data, said processing comprising simultaneously fitting said optical measured data for the multiple measured stacks with said theoretical model and extracting said at least one common parameter, thereby enabling to characterize the properties of the multi-layer structure within the single article;
    wherein any of said providing, performing, and processing are implemented in a machine.

2. The method of claim 1, wherein said at least two different stacks include stacks associated with different locations, respectively, on the article.

3. The method of claim 1, wherein said at least two different stacks include stacks associated with the same location on the article and corresponding to different process steps applied to the article.

4. The method of claim 1, wherein said at least two different stacks include at least one patterned site.

5. The method of claim 1, wherein the geometrical parameters include layer thickness parameters.

6. The method of claim 1, wherein the geometrical parameters include pattern parameters.

7. The method of claim 6, wherein the pattern parameters include at least one of the following: pitch, critical dimension, feature shape, feature height, duty cycle.

8. The method of claim 7, wherein the feature shape comprise at least one of wall angle, wall shape, and rounding of the pattern feature.

9. The method of claim 6, wherein the different stacks include periodic patterns with one or more different pattern parameters.

10. The method of claim 1, wherein said optical measurements comprise spectral reflectometry and/or ellipsometry based measurements.

11. The method of claim 1, wherein said different stacks are located within a product region of the article.

12. The method of claim 1, wherein said optical measurements are performed in several steps of a process of manufacturing said article.

13. The method of claim 1, wherein the selection of the stacks for measurements and/or the parameters is performed on existing sites present on a mask.

14. The method of claim 1, wherein said correlation analysis comprises covariance analysis technique.

15. The method of claim 1, wherein said providing of the theoretical model comprises selecting an appropriate theoretical model enabling to match the measured data obtainable by said optical measurements.

16. The method of claim 1, wherein said providing of the theoretical model comprises modeling the pattern using trapezoidal shapes.

17. The method of claim 1, wherein the simultaneous fitting of said optical measured data is a multi-parameter fitting procedure.

18. The method of claim 1, wherein said processing comprises fitting the optical measured data for at least one separate stack from the multiple measured stacks with a corresponding theoretical model, and extracting at least one parameter of said at least one separate stack; and performing said simultaneously fitting using said at least one parameter of the separate stack.

19. The method of claim 1, comprising optimizing the theoretical model, said optimizing comprising ranking the common parameters in accordance with their estimated contribution to a degree of fit between the theoretical model and the optical measured data.

20. The method of claim 19, wherein the estimated contribution comprises the model sensitivity to the parameter variation and/or correlation between the common parameters.

* * * * *